(12) United States Patent
Chasser et al.

(10) Patent No.: US 6,737,163 B2
(45) Date of Patent: May 18, 2004

(54) LOW-CURE POWDER COATINGS AND METHODS FOR USING THE SAME

(75) Inventors: Anthony M. Chasser, Allison Park, PA (US); Shawn P. Duffy, Cheswick, PA (US); Ronald R. Ambrose, Pittsburgh, PA (US)

(73) Assignee: PPG Industries Ohio, Inc., Cleveland, OH (US)

( * ) Notice: Subject to any disclaimer, the term of this patent is extended or adjusted under 35 U.S.C. 154(b) by 44 days.

(21) Appl. No.: 10/160,466

(22) Filed: May 31, 2002

(65) Prior Publication Data

US 2003/0228468 A1 Dec. 11, 2003

(51) Int. Cl.⁷ .............................................. B32B 27/38
(52) U.S. Cl. .................... 428/418; 428/413; 428/423.1; 427/386; 427/388.1; 528/61; 528/211; 528/905; 525/423
(58) Field of Search ................................. 428/413, 418, 428/423.1; 427/386, 388.1, 391, 393; 528/61, 211, 905; 525/423

(56) References Cited

U.S. PATENT DOCUMENTS

| | | | |
|---|---|---|---|
| 4,324,739 A | 4/1982 | Zondler et al. | 260/465.4 |
| 5,569,733 A | 10/1996 | Donnelly et al. | 528/61 |
| 5,714,206 A | 2/1998 | Daly et al. | 427/475 |
| 5,907,020 A | 5/1999 | Correll et al. | 525/526 |
| 6,077,610 A | 6/2000 | Correll et al. | 428/413 |

OTHER PUBLICATIONS

Abstract, DE19512479, Meckel, Oct. 10, 1996.
Abstract, GP 0594133, Sakata et al., Apr. 27, 1994.

Primary Examiner—Robert Dawson
Assistant Examiner—Christopher M Keehan
(74) Attorney, Agent, or Firm—Diane R. Meyers

(57) ABSTRACT

Low-cure powder coating compositions are disclosed. The compositions comprise a polyepoxide and a material having the structure

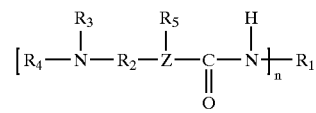

wherein $R_1$ is an organic radical having 6 to 25 carbon atoms; $R_2$ is an organic radical having 1 to 20 carbon atoms; $R_3$ and $R_4$ are independently alkyl or phenyl groups having 1 to 8 carbon atoms; Z is oxygen or nitrogen, and when Z is oxygen $R_5$ is absent and when Z is nitrogen $R_5$ is hydrogen or is

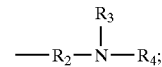

and n is 1 to 4. The material can optionally be reacted with an acidic hydrogen-containing compound. The compositions are curable without the use of crosslinking agents or accelerators. Methods for coating a substrate using these compositions, and substrates coated thereby, are also disclosed, as are additional catalysts useful for the same purpose.

23 Claims, No Drawings

LOW-CURE POWDER COATINGS AND METHODS FOR USING THE SAME

FIELD OF THE INVENTION

The present invention relates to powder coating compositions; more particularly, the present invention relates to low temperature cure thermosetting powder coating compositions. The compositions consistently produce coatings having desirable performance properties when cured, and that are stable when uncured.

BACKGROUND OF THE INVENTION

Coating compositions have long been used to provide the surface of articles with certain desired physical characteristics, such as color, gloss and durability. Many coating compositions rely on a liquid carrier, which evaporates after the composition is applied. In recent years, powder coatings have become increasingly popular; because these coatings are inherently low in volatile organic content (VOCs), their use reduces air emissions during the application and curing processes as compared with liquid coatings.

Powder coatings are typically cured by heating the coated substrate to an elevated temperature. These temperatures almost always exceed 125° C., and commonly reach about 190° C. to 205° C. During the curing process, the powder particles melt and spread, and the components of the powder coating react. In addition to not emitting any VOCs into the environment during the application or curing processes, powder coating systems are extremely efficient since there is essentially no waste (i.e., application yield is approximately 100 percent). Because of the relatively high (i.e., greater than 125° C.) cure temperatures of most powder coatings, their use, for practical purposes, is often limited to substrates that can withstand such high temperatures or that can be heated to an appropriate temperature long enough for cure to occur.

Despite the desirability of low-cure powder compositions, two problems have prevented their widespread production and use—their mechanical stability and their chemical stability. Powders that use resins with a glass transition temperature ("Tg") lower than 60° C. usually encounter package stability problems, especially if exposed to prolonged heat exposure, and become fused, sintered or clumpy within days. Similarly, prolonged heat exposure can destroy the chemical stability of a powder if it includes crosslinkers that react at temperatures below about 170° C.; if a crosslinker with a lower cure temperature is used, cure may be initiated during storage even though the film has not been formed. The premature gelation that occurs in these powder formulations results in coatings having shortened gel times. It is not unusual for low-cure powders to lose >50 percent of their gel time as a result of the premature gelation.

Problems encountered when a powder loses either mechanical or chemical stability can be severe. Poor mechanical stability creates obvious handling, application and appearance issues. Poor chemical stability creates subtler yet just as problematic issues. For example, a powder that has poor chemical stability will fluidize and apply like virgin powder, but because it has advanced in reactivity (i.e. undergone some premature gelation), it demonstrates restricted flow or no flow at all during cure. The result can be a coating having an "orange peel" appearance, a rough texture or gel bodies.

Ideally, a powder should not lose its handling properties under elevated temperature storage and the gel time should remain the same as that of the virgin material. To achieve this, powders are typically formulated with resins having a Tg greater than about 60° C. and/or crosslinkers that react at temperatures of about 170° C. or greater. Such powders, however, are not low cure. Low-cure powders having lower Tg resins or lower temperature crosslinkers can require expensive storage under refrigeration and air-conditioned application facilities to overcome inherent lack of stability, or must be prepared using special techniques.

Thus, there is a need in the coatings art for low-cure powder coatings having a wide range of application, which also have an acceptable level of durability when cured on the finished product and good stability at room temperature.

SUMMARY OF THE INVENTION

The present invention is directed to powder coating compositions generally comprising a tertiary aminourea compound, a tertiary aminourethane compound, or mixtures thereof, and a film-forming polyepoxide resin. It has been surprisingly discovered that polyepoxide resins, when used with the present tertiary aminourea and/or aminourethane compositions, cure to form a suitable coating without the aid of crosslinkers, accelerators, or other additives typically regarded in the art as being necessary to cure a polyepoxide resin. The cured coatings that result from the present compositions have performance properties that are at least as good as powder coating compositions prepared with the same polyepoxides and conventional curing agents, but lacking the tertiary aminourea or aminourethane compositions described herein. Significantly, this desirable result is achieved by using curing temperatures much lower than those used for conventional products. Accordingly, the present compositions are low-cure. "Low-cure" as used herein refers to powder coating compositions that cure at a temperature between about 80° C. and 125° C. However, the present invention is not limited to this temperature range and also provides cured films at temperatures up to and even greater than 190° C.

As a result of being low-cure, the present compositions can be used on substrates that are not appropriately exposed to temperatures greater than about 125° C. Examples include, but are not limited to, plastics such as thermoset and thermoplastic compositions, wood, and pieces of thick metal that cannot be heated above about 95° C. because of their size. Also suitable are articles of manufacture that include a variety of substrates; for example, motors that contain both metal and rubber components can be suitably coated using the present, low-cure powder compositions.

The present compositions also overcome some of the difficulties that have been observed with other powder coating compositions, particularly other low-cure powders. For example, the present powder compositions are storage stable, and reduce, if not eliminate, the problems with chemical and mechanical stability seen with other low-cure powder compositions. The present compositions can be stored at room temperature, and they do not continue to catalyze the reaction of the polyepoxide molecules after the removal of heat. Moreover, the present powder compositions can be prepared using standard methods known in the art for preparing powder coating compositions; no special processing or handling is needed. Thus, the present compositions provide a significant advance in the low-cure powder coatings art.

Methods for coating substrates using the present powder compositions, and substrates coated thereby, are also within the scope of the present invention. Various low-cure catalysts are also included in the present invention.

DETAILED DESCRIPTION OF THE INVENTION

The present invention is directed to a powder coating composition comprising: (a) a material having the structure of Formula I:

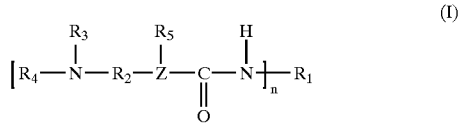

wherein $R_1$ is an organic radical having 6 to 25 carbon atoms, $R_2$ is an organic radical having 1 to 20 carbon atoms; $R_3$ and $R_4$ are independently alkyl or phenyl groups having 1 to 8 carbon atoms; Z is oxygen or nitrogen and when Z is oxygen $R_5$ is absent and when Z is nitrogen $R_5$ is hydrogen or

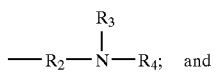

and n is 1 to 4; and (b) a polyepoxide. It will be understood that when Z is oxygen a tertiary aminourethane compound is represented and when Z is nitrogen, Formula I depicts a tertiary aminourea compound. It will be further understood that when $R_5$ is

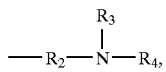

there will be two each of $R_2$, $R_3$ and $R_4$. Each $R_2$, each $R_3$ and each $R_4$ can be the same or different as the other $R_2$, $R_3$ or $R_4$. For example, one $R_2$ can have one carbon and the other have two carbons, and the like.

The material of Formula I can be an oligomer wherein $R_1$ is a monovalent, divalent, trivalent or tetravalent organic radical; divalent radicals are particularly suitable. The $R_1$ radical can be aliphatic, such as hexamethylene, cycloaliphatic such as cyclohexylene, substituted cycloaliphatic such as 1,1,3,3-tetramethylcyclohexylene, or aromatic such as phenylene. Substituted cycloaliphatics are particularly suitable, especially 1,1,3,3-tetramethylcyclohexylene. Examples of suitable $R_2$ moieties include ethylene, n-propylene, and iso- and n-butylene. In a particularly suitable composition, Z is nitrogen, $R_1$ is 1,1,3,3-tetramethylcyclohexylene, $R_2$ is propylene, $R_3$ and $R_4$ are both methyl groups, $R_5$ is hydrogen and n is 2.

The material of component (a) can be prepared by reacting an organic polyisocyanate, particularly diisocyanate, with an amine containing a primary or secondary amine group and a tertiary amine group for the aminourea embodiment or with an alcohol or polyol containing a tertiary amine for the aminourethane embodiment. Suitable polyisocyanates include aliphatic, cycloaliphatic, or aromatic polyisocyanates. Diisocyanates are particularly suitable, although higher polyisocyanates can be used. Examples of suitable aromatic diisocyanates are 4,4'-diphenylmethane diisocyanate, 1,3-bis(1-isocyanato-1-methylethyl)benzene and derivatives thereof, and toluene diisocyanate. Examples of suitable aliphatic diisocyanates are straight chain aliphatic diisocyanates such as 1,6-hexamethylene diisocyanate and cycloaliphatic diisocyanates including isophorone diisocyanate and 4,4'-methylene-bis-(cyclohexyl isocyanate).

Examples of suitable higher polyisocyanates are 1,2,4-benzene triisocyanate, polymethylene polyphenyl isocyanate and the isocyanurate of isophorone diisocyanate. Isophorone diisocyanate is especially suitable.

Examples of amines containing a primary or secondary amine group and a tertiary amine group are dimethylaminopropylamine, bis(dimethylamino) propylamine and 2-amino-5-diethylaminopentane. An example of an alcohol containing a tertiary amine is dimethylaminopropanol. Dimethylaminopropylamine is particularly suitable.

The diamine or amino alcohol and polyisocyanate are combined in an equivalent ratio of about 1:1. The diamine is heated to about 50° C., and the polyisocyanate is added over a period of time in the range of about one to two hours, usually about two hours. The amino alcohol typically should be heated to about 80° C. before the polyisocyanate is added. The temperature of the reaction mixture generally increases and is held at an elevated temperature, such as 130° C. to 170° C., until the polyisocyanate is completely reacted.

The present invention is further directed to a curable powder composition comprising a polyepoxide and the reaction product of a polyisocyanate and either an amine comprising a primary or secondary amine group and a tertiary amine, or an alcohol or polyol containing a tertiary amine. Suitable amines and alcohols/polyols, and the method for preparing such a reaction product, are described above.

In one embodiment, the material of component (a) further comprises an acidic hydrogen-containing compound; for example, component (a) can comprise the reaction product of (i) a compound having Formula I and (ii) an acidic hydrogen-containing compound. The acidic hydrogen-containing compound of (ii) may be a carboxylic acid, a phenolic compound, a polyester, a polyurethane or an acrylic polymer. Phenolic compounds, especially polyphenols, are particularly suitable. Examples of suitable acidic hydrogen-containing compounds include benzoic acid, dodecanedioic acid, azelaic acid, itaconic acid, sebacic acid, and adipic acid. Suitable phenols include phenol itself and polyphenols such as resorcinol, catechol, hydroquinone, bis(4-hydroxyphenyl)-2,2-propane (Bisphenol A), bis(4-hydroxyphenyl)-1,1-isobutane, bis(4-hydroxyphenyl)-1,1-ethane, bis(2-hydroxyphenyl)-methane, 4,4'-dihydroxybenzophenone, and 1,5-dihydroxynaphthalene. Bisphenol A is especially suitable.

The reaction product used in the coatings of the present invention can be prepared by mixing the material having Formula I of (i) with the acidic hydrogen-containing compound of (ii) in an equivalent ratio of about 1:1 to 1:2, such as about 1:1.87. The material of (i) is typically heated to a temperature of about 140 to 180° C. and the acidic hydrogen-containing compound of (ii) is added. The reaction mixture is then usually held at the elevated temperature until it turns clear, indicating homogeneity of the reaction mixture. The reaction mixture is then allowed to cool.

Component (a) in the present compositions, both with and without the acidic hydrogen-containing compound, is used as a catalyst, and typically has a melting point of between about 23° C. and 150° C., such as between about 50 and 100C. This range of melting points helps prevent any curing from taking place in the composition before the application of heat. This improves the long-term stability of curable compositions in which component (a) is used. The melting point of the catalyst is typically not so high, however, that the present compositions lose their characterization as "low-cure". It is therefore desirable that the catalyst used in the present compositions have a melting point of between about 23° C. and 150° C.; if the melting point were too far above this number, the composition might not cure in the desired manner, and at temperatures too much below this temperature, the composition may not be as stable.

The polyepoxides used in the present compositions are those that are suitable for use in powder coatings, such as those that contain at least two 1,2-epoxide groups per molecule. In general, the epoxy equivalent weight can range from about 180 to about 4000 based on solids of the polyepoxide, such as between about 500 and 1000. The polyepoxides may be saturated or unsaturated, and may be aliphatic, alicyclic, aromatic, or heterocyclic. They may contain substituents such as halogens, hydroxyl groups, and ether groups.

Suitable classes of polyepoxides include epoxy ethers obtained by reacting an epihalohydrin such as epichlorohydrin with a polyphenol in the presence of an alkali. Suitable polyphenols include resorcinol, catechol, hydroquinone, bis(4-hydroxyphenyl)-2,2-propane (Bisphenol A), bis(4-hydroxyphenyl)-1,1-isobutane, bis(4-hydroxyphenyl)-1,1-ethane, bis(2-hydroxyphenyl)-methane, 4,4-dihydroxybenzophenone, and 1,5-dihydroxynaphthalene. The diglycidyl ether of Bisphenol A is especially suitable.

Other suitable polyepoxides include polyglycidyl ethers of polyhydric alcohols. These compounds may be derived from polyhydric alcohols such as ethylene glycol, propylene glycol, butylene glycol, 1,6-hexylene glycol, neopentyl glycol, diethylene glycol, glycerol, trimethylol propane, and pentaerythritol. These compounds may also be derived from polymeric polyols such as polypropylene glycol.

Examples of other suitable polyepoxides include polyglycidyl esters of polycarboxylic acids. These compounds may be formed by reacting epichlorohydrin or another epoxy material with an aliphatic or aromatic polycarboxylic acid such as succinic acid, adipic acid, azelaic acid, sebacic acid, maleic acid, 2,6-naphthalene dicarboxylic acid, fumaric acid, phthalic acid, tetrahydrophthalic acid, hexahydrophthalic acid, or trimellitic acid. Dimerized unsaturated fatty acids containing about 36 carbon atoms (Dimer Acid) and polymeric polycarboxylic acids such as carboxyl terminated acrylonitrile-butadiene rubber may also be used in the formation of these polyglycidyl esters of polycarboxylic acids.

Polyepoxides derived from the epoxidation of an olefinically unsaturated alicyclic compound are also suitable for use in the curable composition of the present invention. These polyepoxides are nonphenolic and are obtained by epoxidation of alicyclic olefins with, for example, oxygen, perbenzoic acid, acid-aldehyde monoperacetate, or peracetic acid. Such polyepoxides include the epoxy alicyclic ethers and esters well known in the art.

Other suitable polyepoxides include epoxy novolac resins. These resins are obtained by reacting an epihalohydrin with the condensation product of aldehyde and monohydric or polyhydric phenols. A typical example is the reaction product of epichlorohydrin with a phenol-formaldehyde condensate.

The curable composition of the present invention may contain one polyepoxide or mixtures of polyepoxides.

Typically, the polyepoxide is present in the curable composition of the present invention in a range of from about 20 to about 90 percent, such as about 30 to 60 percent, based upon total weight of the curable composition. The catalyst or reaction product is typically present in the compositions of the invention in a range of from about 0.5 to 10 weight percent, such as 3 to 5 weight percent. It is expected that the rate of cure increases as the concentration of catalyst increases, and that these increases are directly proportional. It is surprising, however, that no decrease in chemical or mechanical stability is noted as higher catalyst levels are used; stability often behaves inversely proportional to reactivity, in that as reactivity increases, stability decreases. This maintained stability with increased reactivity is yet another advantage of the present invention.

The powder coating compositions of the present invention may optionally contain additives such as waxes for flow and wetting, flow control agents, such as poly(2-ethylhexyl) acrylate, degassing additives such as benzoin and MicroWax C, adjuvant resin to modify and optimize coating properties, antioxidants and the like. These optional additives, when used, can be present in amounts up to 10 weight percent, based on total weight of the coating composition, and if used will typically comprise about 1 to 5 weight percent. Any of various pigments standardly used in the powder coatings art can also be included. Pigment weight can be up to 80 percent of the weight of the entire coating and usually is around 35 weight percent of the coating. The compositions can further comprise a plurality of particles, such as organic or inorganic particles, or mixtures thereof, that contribute to the mar and/or scratch resistance of the coatings. Such particles are described in Ser. No. 10/007,149, filed on Dec. 5, 2001, which is hereby incorporated by reference. Pigments or solid additives in nanoparticulate form can also be included in the present compositions for the same purpose.

It is both a significant and surprising discovery that the present compositions will cure at low temperatures in the absence of any additional components, such as a crosslinking agent and/or accelerator typically used in conjunction with polyepoxide resins, and thought to be required. In some cases, the use of a crosslinker and accelerator can actually raise the temperature required to cure the polyepoxide, so their use may be undesirable for a low-cure product. Although the inventors do not wish to be bound by any mechanism, it is believed that the reaction product or catalyst used in the present composition catalyzes the reaction of the polyepoxide molecules with themselves. This is in contrast to the standard mechanism of action, in which such a catalyst would be expected to facilitate the reaction between the polyepoxide and crosslinking agent. Thus, the present invention is further directed to a method for initiating self cure of a polyepoxide by adding any of the catalysts described herein to a composition comprising a polyepoxide.

Notwithstanding the lack of a crosslinking agent, the crosslinked density of the present coating compositions can still be controlled to a large extent. This is accomplished by controlling the amount of catalyst added to the composition. Higher amounts of catalyst usually gel the films faster and crosslink the films more efficiently. In addition, there is a cost savings associated with the elimination of crosslinkers and accelerators, and the ability to cure at a lower temperature. Significantly, the present crosslinker-free and accelerator-free compositions result, upon curing, in coating compositions that have performance properties at least equal to that of conventional powder coatings in which a polyepoxide and conventional crosslinker are used. This refers to the ability to maintain appearance as measured by a number of properties relevant to cured coatings, such as resistance to solvents, pencil hardness, and impact and corrosion resistance.

The present compositions can be prepared by standard methods known in the art. For example, the components are first thoroughly mixed to ensure spatial homogeneity of the ingredients. The composition is then intimately melt kneaded in an extruder. Typical zone temperatures during extrusion range from 40° C. to 125° C., such as 45° C. to 100° C. The exiting extrudate is rapidly cooled to terminate polymerization. The resulting chip is then micronized into powder with an average particle size of 0.1 to 200 microns, such as 1 to 100 microns. Comminution methods are well known, comminution can be accomplished, for example, by air-classifying mills, impact mills, ball mills, or other fracture-induced mechanisms. Post additives that improve fluidization of the powder mass and/or improve the resistance to impact fusion may be incorporated into the final product before or after micronization. As noted, the use of standard powder coating preparation methods is another advantage of the present invention.

Accordingly, the present invention is further directed to powder coating compositions that cure at a temperature of between 80° C. and 125° C. comprising a resin and curing agent and wherein substantially all of the curing agent is extruded with the resin. "Substantially all" means the amount of curing agent needed to completely cure the resin. The present invention is further directed to such compositions that do not cure at temperatures below about 70° C., such as at ambient temperature, like many commercially available low-cure products.

Typically, the present powder coatings will have average particle sizes that range between 15 and 200 microns, such as between about 25 and 50 microns.

The powder coating compositions of the present invention can be applied to a substrate in any number of ways, most often by electrostatic spraying. The powder coating can be applied in a single sweep or in several passes to provide a film having a thickness after cure of from about 1 to 10 mils (25 to 250 microns), usually about 2 to 4 mils (50 to 100 microns). Other standard methods for coating application can also be employed.

After application, the present compositions may be cured by heating to a temperature of between about 80° C. and 190° C., preferably between about 80° C. and 125° C., for a period ranging from about 3 minutes to 30 minutes, such as 15 to 20 minutes. Heating can be effected by any means known in the art, typically by placing the coated substrate in an oven. IR radiation can also be used to heat cure the coated substrates.

Accordingly, the present invention is further directed to a method for coating a substrate comprising applying to the substrate one or more of the coating compositions described herein and curing the coating at a temperature of between about 80° C. and 190° C., such as between about 80° C. and 125° C. or between about 105° C. and 120° C. In such a method, the polyepoxide will self-cure, or react with itself by homopolymerization; this reaction is catalyzed by the present tertiary aminourea or tertiary aminourethane compositions. Accordingly, the present invention is further directed to a cured coating layer comprising a polyepoxide and one or more of the catalysts described herein, wherein the polyepoxide is self-cured.

A number of substrates are suitable for coating according to the methods of the present invention, including plastics such as thermosets or thermoplastics, cardboard, paper, wood, metal, particleboard and medium density fiberboard or mixtures thereof. Substrates coated according to the present methods are also within the scope of the present invention.

The present invention is further directed to a catalyst composition that is the reaction product of:

(i) a material having the structure of Formula II and (ii) an acidic hydrogen-containing compound

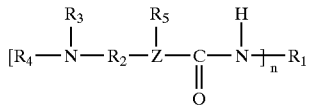

(II)

For Formula II, $R_1$ is an organic radical having 6 to 25 carbon atoms, $R_2$ is an organic radical having 1 to 20 carbon atoms; $R_3$ and $R_4$ are independently alkyl or phenyl groups having 1 to 8 carbon atoms; Z is oxygen or nitrogen and when Z is oxygen $R_5$ is absent and when Z is nitrogen $R_5$ is hydrogen or

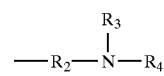

and n is 1 to 4, but when Z is nitrogen, $R_2$ is an alkylene having between 1 and 4 carbon atoms, and $R_3$ and $R_4$ are both alkyl groups having between 1 and 4 carbons, $R_5$ is not hydrogen.

The present invention is directed to yet another catalyst composition comprising the compound of Formula I as described above, wherein the composition does not include an acidic hydrogen-containing compound. It has surprisingly discovered that compounds having Formula I function as low-cure catalysts even in the absence of acidic hydrogen-containing compounds.

As used herein, unless otherwise expressly specified, all numbers such as those expressing values, ranges, amounts or percentages may be read as if prefaced by the word "about", even if the term does not expressly appear. Also, any numerical range recited herein is intended to include all sub-ranges subsumed therein. As used herein, the term "polymer" refers to oligomers and both homopolymers and copolymers; the prefix "poly" refers to two or more.

EXAMPLES

The following examples are intended to illustrate the invention, and should not be construed as limiting the invention in any way.

Example 1

The following ingredients were used to prepare a catalyst of Formula I, wherein an acidic hydrogen-containing compound is used.

| Ingredient | Weight, g | Equivalents | Percent by weight |
|---|---|---|---|
| Dimethylaminopropylamine | 204.4 | 1.000 | 23.95% |
| Isophorone diisocyanate ("IPDI")[1] | 222.2 | 1.000 | 26.05% |
| Bisphenol A ("BPA")[2] | 426.6 | 3.74 | 50.00% |

[1]Available from Hüls America, Inc.
[2]4,4'-Isopropylidenediphenol available from Dow Chemical Co.

The dimethylaminopropylamine was charged to a suitable reactor and heated to 50° C. The IPDI was added through an addition funnel over a period of two hours. The temperature of the reaction mixture was allowed to increase to 90° C. during the addition. After the addition was complete the reaction mixture was heated to 130° C. and held at that temperature until infrared analysis indicated consumption of the isocyanate. The reaction mixture was then heated to 160° C. and the Bisphenol A was added. The reaction mixture was held at 160° C. until the solution turned clear, indicating complete melting of the Bisphenol A. The reaction mixture was poured out hot and allowed to cool and solidify. The final solid product had a solids content of about 98 percent and a number average molecular weight of 336 as measured by gel permeation chromatography using polystyrene as a standard.

Example 2

The following ingredients were used to prepare a catalyst of Formula I, wherein an acidic hydrogen-containing compound is not used.

| Ingredient | Weight, g | Equivalents | Percent by weight |
|---|---|---|---|
| Dimethylaminopropylamine | 204.4 | 1.000 | 47.9% |
| Isophorone diisocyanate (IPDI) | 222.2 | 1.000 | 52.1% |

The dimethylaminopropylamine was charged to a suitable reactor and heated to 50° C. The IPDI was added through an addition funnel over a period of two hours. The temperature of the reaction mixture was allowed to increase to 90° C. during the addition. After the addition was complete the reaction mixture was heated to 130° C. and held at that temperature until infrared analysis indicated consumption of the isocyanate. The reaction mixture was poured out hot and allowed to cool and solidify. The final solid product had a solids content of about 98 percent and a number average molecular weight of 336 as measured by gel permeation chromatography using polystyrene as a standard.

Example 3

Samples 1 to 4 were prepared using the components and amounts shown in TABLE 1, including the products prepared according to Examples 1 and 2. The coatings were prepared by premixing the ingredients in a three-blade mixer rotating at 3500 rpm. The premix was then extruded in a 19 mm dual screw extruder operating at a temperature of 80° C. The extrudate was rapidly cooled and pressed into chip. The chip was micronized to an average particle size of 35 microns using a Hosokawa Air-Classifying Mill (ACM).

TABLE 1

| | Sample 1 | Sample 2 | Sample 3 | Sample 4 |
|---|---|---|---|---|
| EPON 1001[3] | | | 340 g | 340 g |
| EPON 2002[4] | | | 140 g | 140 g |
| DER 642[5] | | 480 g | | |
| PD 9060 (GMA Acrylic)[6] | 480 g | | | |
| Product of Example 1 | 15 g | 15 g | 15 g | |
| Product of Example 2 | | | | 7.5 g |
| Benzoin[7] | 4 g | 4 g | 4 g | 4 g |
| Modaflow[8] | 9 g | 9 g | 9 g | 9 g |
| Goresil 210[9] | 50 g | 50 g | 50 g | 50 g |
| $TiO_2$ | 150 g | 150 g | 150 g | 150 g |

[3]EPON 1001 is a BPA epoxy, standard hybrid type, with an EW = 550 from Resolution Performance Products.
[4]EPON 2002 is a BPA epoxy, standard hybrid type, with an EW = 750 from Resolution Performance Products.
[5]DER 642 is a NOVALAC resin from Dow Chemical.
[6]PD 9060 is a GMA Acrylic resin from Anderson Development
[7]Added as a degasser.

TABLE 1-continued

| | Sample 1 | Sample 2 | Sample 3 | Sample 4 |
|---|---|---|---|---|

[8]An acrylic copolymer flow additive, anti-crater additive, from Solutia, Inc.
[9]Silica particles, average particle size 2 microns, largest particle size 10 microns, from CED Process Minerals, Inc.

The coatings were sprayed onto Bonderite 1000 steel panels and cured at 115.6° C. for 25 minutes. Following cure, the panels were subjected to a number of tests standard in the industry for testing coatings. Tests and results are shown in TABLE 2.

TABLE 2

| | Sample 1 | Sample 2 | Sample 3 | Sample 4 |
|---|---|---|---|---|
| 100 MEK double rubs[10] | No scuff | No scuff | No scuff | No scuff |
| Impact Reverse/Direct[11] | <20/<20 | 70/100 | 160/160 | 160/160 |
| QUV 340 400 hrs[12] | 60 → 60 | 60 → 20 | 60 → 15 | 60 → 15 |
| Appearance[13] | PCI = 1 | PCI = 7 | PCI = 7 | PCI = 6 |
| Gel time[14] | 6:00 | 3:00 | 3:00 | 3:00 |
| 1000 hrs salt fog 100F[15] | 2 mm creep | <1 mm creep | <1 mm creep | <1 mm creep |
| 1000 hrs cond hum 100F[16] | <1 mm creep | <1 mm creep | <1 mm creep | <1 mm creep |
| Powder stability (chemical)[17] | 6:00 | 3:00 | 3:00 | 3:00 |

[10]Powder Coatings Institute ("PCI") #8 Recommended Procedure. ("No scuff" means the coating is fully cured.)
[11]ASTM D2794 (Range <20 to 160 in*lbs.; 160 in*lbs = full flexibility.)
[12]ASTM D4587 (results reported in 200 gloss readings taken initially → after 400 hours of QUV exposure.)
[13]PCI visual standards (Range 1 to 10 - 10 being the smoothest.)
[14]PCI #6 Recommended Procedure (gel time reported in minutes:seconds.)
[15]ASTM B117 (<1 mm = no salt fog effect.)
[16]ASTM D1735 (<1 mm creep = no humidity effect.)
[17]PCI #1 Recommended Procedure at 32° C. (stability reported in minutes:seconds.)

The results in TABLE 2 confirm that a variety of polyepoxy resins can be cured at low temperature according to the present invention. The acrylic sample (Sample 1) performed as would be expected in the impact and QUV testing—that is, not as well on the former and very well on the latter. Bisphenol A epoxies (Samples 3 and 4) work especially well with the present invention providing the highest level of impact resistance, humidity and salt fog resistance, and chemical resistance; although QUV results were lower than with other samples, this would be expected with this type of resin. One skilled in the art could choose the appropriate resin based on the desired qualities of the cured coating, using the present catalysts to effect cure at low temperatures.

Example 4

Sample 3 prepared as described above was tested for stability using standard techniques as discussed below. The stability of Sample 3 was also compared with the stability of Sample 5, prepared in the same manner as Sample 3 except using three grams of 2-methyl imidazole as the catalyst instead of the catalyst prepared according to Example 1. A standard polyepoxide resin cured with an acid polyester was also compared (PCF 80147, commercially available from PPG Industries, Inc.). The coatings were applied as described in Example 2. However, the commercially available product was cured at a higher temperature (162.8° C.) compared to 115.6° C. for Sample 3 and Sample 5.

TABLE 3

|  | PCF 80147 | Sample 3 | Sample 5 |
|---|---|---|---|
| Mechanical Stability One week at 32° C. | Excellent | Excellent | Excellent |
| Chemical stability Initial Gel @ 145° C. | 4:00 | 3:00 | 1:30 |
| Gel after One Week @ 32° C. | 4:00 | 3:00 | :40 |
| 100 MEK Double rubs | No Scuff | No Scuff | No Scuff |

The chemical stability and mechanical stability tests were identical, and were performed by placing virgin, free-flowing powder in a sealed jar and setting the jar in a water bath heated (PCI #1 Recommended Procedure, as described in TABLE 2). After one week the samples were evaluated for mechanical stability using a visual ranking. A free-flowing powder is excellent; the ranking standardly used in the industry is as follows: excellent>good>cakey>clumpy>fused>sintered. All samples had an excellent mechanical stability.

After the visual ranking for mechanical stability, gel times of the aged powder were taken as per PCI #6 Recommended Procedure to assess the chemical stability of the powder coating. A slower gel time translates to advancement in molecular weight. A powder coating should not have molecular weight advancement during storage. As shown in TABLE 3, only Sample 5 (2-methyl imidazole catalyst) showed advancement; the commercial product and the product of the present invention did not advance over time.

Solvent cure (100 MEK double rubs—PCI #8 Recommended Procedure) was used as an indication of film cure. When a film has excellent solvent resistance, that is a good indication that complete cure has occurred. Sample 3 of the present invention underwent complete cure just as the other samples tested.

Thus, the low-cure composition of the present invention performed equal to a commercially available high cure product using conventional crosslinkers and performed better than a sample using a low temperature curing agent outside the scope of the present invention.

Whereas particular embodiments of this invention have been described above for purposes of illustration, it will be evident to those skilled in the art the numerous variations of the details of the present invention may be made without departing from the invention as defined in the appended claims.

Therefore, what is claimed is:

1. A curable powder composition comprising:

(a) a material having the structure:

$$[R_4-\underset{\underset{R_3}{|}}{N}-R_2-\underset{\underset{R_5}{|}}{Z}-\underset{\underset{O}{\|}}{C}-\underset{\underset{H}{|}}{N}]_n-R_1$$

wherein $R_1$ is an organic radical having 6 to 25 carbon atoms, $R_2$ is an organic radical having 1 to 20 carbon atoms; $R_3$ and $R_4$ are independently alkyl or phenyl groups having 1 to 8 carbon atoms; Z is oxygen or nitrogen and when Z is oxygen, $R_5$ is absent and when Z is nitrogen, $R_5$ is hydrogen or $$-R_2-\underset{\underset{R_3}{|}}{N}-R_4$$

and when $$R_5 \text{ is } -R_2-\underset{\underset{R_3}{|}}{N}-R_4,$$

each $R_2$,
each $R_3$ and each $R_4$ are the same or different; an n is 1 to 4; and (b) a polyepoxide;

wherein the powder composition cures in the absence of any addition component.

2. The powder composition of claim 1, wherein said composition cures at a temperature of between 80° C. and 125° C.

3. The powder composition of claim 2, wherein said composition cures at a temperature of between 105° C. and 120° C.

4. The powder composition of claim 1, wherein said composition cures at a temperature greater than 125° C.

5. The powder composition of claim 1, wherein Z is nitrogen and $R_5$ is hydrogen.

6. The composition of claim 5, wherein $R_1$ is 1,1,3,3-tetramethylcyclohexylene.

7. The composition of claim 5, wherein $R_2$ is n-propylene.

8. The composition of claim 5, wherein $R_3$ and $R_4$ are methyl.

9. The composition of claim 1, wherein component (a) further comprises an acidic hydrogen-containing compound.

10. The composition of claim 9, wherein the acidic hydrogen-containing compound is a phenolic compound.

11. The composition of claim 10, wherein the phenolic compound is a polyphenol.

12. The composition of claim 11, wherein the polyphenol is bis(4-hydroxyphenyl)-2,2-propane.

13. The composition of claim 1, wherein (a) is present in an amount ranging from about 0.5 to 10 weight percent, and (b) is present in an amount ranging from about 20 to about 90 weight percent, with weight percent being based upon total weight of the composition.

14. The composition of claim 12, wherein (a) is present in an amount ranging from about 3 to 5 weight percent, and (b) is present in an amount ranging from about 30 to about 60 weight percent, with weight percent being based upon total weight of the composition.

15. A method for coating a substrate comprising:

(a) applying to said substrate the powder composition of claim 1; and (b) curing said composition.

16. The method of claim 15, wherein said composition is cured at a temperature of between 80° C. and 125° C.

17. A substrate coated according to the method of claim 15.

18. The substrate of claim 17, wherein said substrate is comprised of a thermoplastic polymer, a thermoset polymer, cardboard, paper, wood, particleboard, medium density fiberboard and/or metal.

19. A cured coating layer comprising:

(a) a material having the structure:

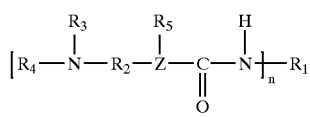

wherein $R_1$ is an organic radical having 6 to 25 carbon atoms, $R_2$ is an organic radical having 1 to 20 carbon atoms; $R_3$ and $R_4$ are independently alkyl or phenyl groups having 1 to 8 carbon atoms; Z is oxygen or nitrogen and when Z is oxygen, $R_5$ is absent and when Z is nitrogen, $R_5$ is hydrogen or

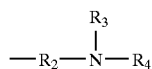

and when $R_5$ is

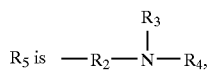

each
$R_2$, each $R_3$ and each $R_4$ the same or different; and n is 1 to 4; and (b) a polyepoxide;
wherein the polyepoxide has reacted with itself during cure.

20. A method for initiating self cure of a polyepoxide resin comprising adding to a composition comprising said resin a catalyst having the structure

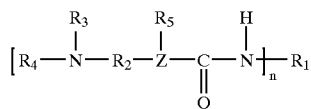

wherein $R_1$ is an organic radical having 6 to 25 carbon atoms, $R_2$ is an organic radical having 1 to 20 carbon atoms; $R_3$ and $R_4$ are independently alkyl or phenyl groups having 1 to 8 carbon atoms; Z is oxygen or nitrogen and when Z is oxygen $R_5$ is absent and when Z is nitrogen, $R_5$ is hydrogen or

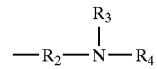

and when

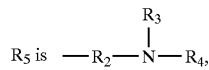

each $R_2$, each $R_3$ and each $R_4$ are the same or different; and n is 1 to 4.

21. The method of claim 20, wherein said catalyst further comprises an acidic hydrogen-containing compound.

22. The composition of claim 1, wherein $R_2$ is alkylene.

23. The composition of claim 1, wherein $R_3$ and $R_4$ are alkyl.

* * * * *